(12) United States Patent
Tseng et al.

(10) Patent No.: US 10,806,467 B2
(45) Date of Patent: Oct. 20, 2020

(54) METHOD OF LOCATING CENTER POSITION AND AXIAL DIRECTION OF DISTAL LOCKING HOLE OF INTRAMEDULLARY NAIL

(71) Applicant: NATIONAL CENTRAL UNIVERSITY, Taoyuan (TW)

(72) Inventors: Ching-Shiow Tseng, Taoyuan (TW); Wei-En Hsu, Hsinchu (TW); Ching-Hsiao Yu, New Taipei (TW)

(73) Assignee: NATIONAL CENTRAL UNIVERSITY, Taoyuan (TW)

( * ) Notice: Subject to any disclaimer, the term of this patent is extended or adjusted under 35 U.S.C. 154(b) by 615 days.

(21) Appl. No.: 15/181,735

(22) Filed: Jun. 14, 2016

(65) Prior Publication Data
US 2017/0172588 A1   Jun. 22, 2017

(30) Foreign Application Priority Data

Dec. 16, 2015 (TW) .............................. 104142377 A (51) Int. Cl.
*A61B 17/17* (2006.01)
(52) U.S. Cl.
CPC ...... *A61B 17/1703* (2013.01); *A61B 17/1725* (2013.01)
(58) Field of Classification Search
CPC ........................ A61B 17/1703; A61B 17/1725
See application file for complete search history.

(56) References Cited

U.S. PATENT DOCUMENTS

2008/0281334 A1\* 11/2008 Zheng ................ A61B 17/1703
606/130
2009/0054910 A1\* 2/2009 Zheng ................ A61B 17/1703
606/130

OTHER PUBLICATIONS

Wei En Hsu, Ching Shiow, Tseng and Hung-Kang Wu; Novel Path Planning Method for C-Arm Image Based Distal Locking of Intramedullary Nails; CAOS201 May 6-20, 2015.
Computer Assisted Orthopaedic Surgery; 15th Annual Meeting of CAOS-International Final Program; CAOS 2015; 24 pgs.
CAOS 2015 Meeting Email; 2 pgs.
Novel Path Planning Method for C-Arm Image Based Distal Locking of Intramedullary Nails; Wei En Hsu et al.; 4 pgs.

(Continued)

*Primary Examiner* — Samuel S Hanna
(74) *Attorney, Agent, or Firm* — Schmeiser, Olsen & Watts, LLP (57) ABSTRACT

A method of locating locking holes of an intramedullary nail includes taking an X-ray image of an intramedullary nail having two locking holes; connecting centroids of the locking hole contours and an X-ray source to define locking hole vectors and axial directions of the locking holes; calculating a first included angle and normal vector perpendicular to vectors connecting the X-ray source and the locking hole contour centroids; defining a cross product of the locking hole vector and the normal vector as a vector connecting centers of the locking holes, and calculating second and third included angles with the vector connecting the locking hole centers and the vectors connecting the X-ray source to the locking hole contour centroids; and locating the locking holes according to the first, second and third included angles, vectors connecting the X-ray source to the locking hole contour centroids, and a distance between the locking holes.

1 Claim, 6 Drawing Sheets

(56) References Cited

OTHER PUBLICATIONS

Novel Path Planning Method for C-Arm Image Based Distal Lockjng of Intramedullary Nails; Wei En Hsu et al.; 1 pg.
CAOS 2015 Meeting Website; 1 pg.
CAOS International Helping Patients by Use of Modern State of the Art Technologies in Orthopaedic; CAOS International; 1 pg.

* cited by examiner

METHOD OF LOCATING CENTER POSITION AND AXIAL DIRECTION OF DISTAL LOCKING HOLE OF INTRAMEDULLARY NAIL

CROSS-REFERENCE TO RELATED APPLICATION

This non-provisional application claims priority under 35 U.S.C. § 119(a) on Patent Application No(s).104142377 filed in Taiwan, R.O.C. on Dec. 16, 2015, the entire contents of which are hereby incorporated by reference.

FIELD OF THE INVENTION

The present invention relates to methods of locating distal locking holes of an intramedullary nail and, more particularly, to a method of locating distal locking holes of an intramedullary nail by using just one X-ray image.

BACKGROUND OF THE INVENTION

Treating a long bone fracture entails implanting an intramedullary nail into the medullary cavity of the bone, drilling the bone at points thereof corresponding in the center positions and axial directions to the distal locking holes of the intramedullary nail, respectively, and driving a locking screw into each drilled hole in the bone and a corresponding one of the distal locking holes so that the bone and the intramedullary nail can be fixed together by the locking screws.

The step of drilling the bone at points thereof corresponding in the center positions and axial directions to the distal locking holes requires locating the locking holes by taking several anterior-posterior and lateral X-ray images thereof. But, the X-ray image-taking process is not only time-consuming but also exposes medical persons and the patient to hazardously high level of radiation, not to mention that the process is not effective in drilling the bone at points thereof corresponding in the center positions and axial directions to the distal locking holes of the intramedullary nail, respectively.

Furthermore, an X-ray image device, namely C-arm, has to move slowly in order to take several anterior-posterior and lateral X-ray images; as a result, it is time-consuming to drill the bone at points thereof corresponding in the center positions and axial directions to the distal locking holes of an intramedullary nail in a fractured bone, respectively.

Furthermore, quick and precise alignment is impossible, because each X-ray image shows the distal locking holes of the intramedullary nail in just one direction which is not enough for the surgeon to quickly and precisely align the locking holes, even though several anterior-posterior and lateral X-ray images of the intramedullary nail are taken.

Accordingly, it is imperative to provide a method of locating a distal locking hole of an intramedullary nail to achieve quick and precise alignment, reduce the number of required X-ray images, and thereby reduce the radiation dose of X-ray which medical persons and the patient might otherwise be exposed to.

SUMMARY OF THE INVENTION

It is an objective of the present invention to provide a method of locating a distal locking hole of an intramedullary nail to achieve quick and precise alignment, reduce the number of required X-ray images, and thereby reduce the radiation dose of X-ray which medical persons and the patient might otherwise be exposed to.

In order to achieve the above and other objectives, the present invention provides a method of locating distal locking holes of an intramedullary nail to enable quick alignment, the method comprising the steps of: S100: taking an X-ray image of an intramedullary nail having at least two parallel distal locking holes with an X-ray image-taking device, wherein the X-ray image shows two locking hole contours; S105: determining whether any one of the locking hole contours is a circle, wherein step S105 is followed by step S110 if the determination is affirmative, and step S105 is followed by step S115 if the determination is negative; S110: connecting the centroid of the locking hole contour and the X-ray emission source of the X-ray image-taking device to define a locking hole vector, wherein the direction of the locking hole vector is defined as axial direction of the distal locking hole, wherein step S110 is followed by step S120; S115: extending the minor axes of the locking hole contours on the X-ray image plane to form an intersection point, connecting the intersection point to the X-ray emission source of the X-ray image-taking device to define a locking hole vector, and defining the direction of the locking hole vector as the axial direction of the distal locking hole, wherein step S115 is followed by step S120; S120: calculating by trigonometric functions a first included angle according to vectors which connect the X-ray emission source to centroids of the locking hole contours, calculating a normal vector by cross product, defining a cross product of the locking hole vector and the normal vector as a vector which connects the centroids of the distal locking holes, and calculating by trigonometric functions a second included angle and a third included angle according to the vector which connects the centroids of the distal locking holes and the vectors which connect the X-ray emission source to the centroids of the locking hole contours, respectively; and S125: locating centers of the distal locking holes relative to the X-ray emission source according to the X-ray emission source, the first included angle, the second included angle, the third included angle, vectors which connect the X-ray emission source to the centroids of the locking hole contours, respectively, and the distance between the centers of the two distal locking holes of the intramedullary nail.

According to the present invention, step S125 is followed by step S130 which entails applying axial directions of the distal locking holes and centroids of the distal locking holes relative to the X-ray emission source to a coordinate system of a drilling device.

According to the present invention, step S102 occurs between step S100 and step S105. Step S102 involves determining whether both the areas defined by the first locking hole contour H1 and second locking hole contour H2 are larger than a predetermined threshold. Go to step S105, if the determination is affirmative. Go to step S100, if the determination is negative.

In conclusion, a method of locating a distal locking hole of an intramedullary nail is effective in not only locating a distal locking hole by using just one X-ray image quickly and precisely but also reducing the number of required X-ray images to thereby reduce the radiation dose of X-ray which medical persons and the patient might otherwise be exposed to.

BRIEF DESCRIPTION OF THE DRAWINGS

Objectives, features, and advantages of the present invention are hereunder illustrated with specific embodiments in conjunction with the accompanying drawings, in which.

DETAILED DESCRIPTION OF THE PREFERRED EMBODIMENTS

Figure 1:
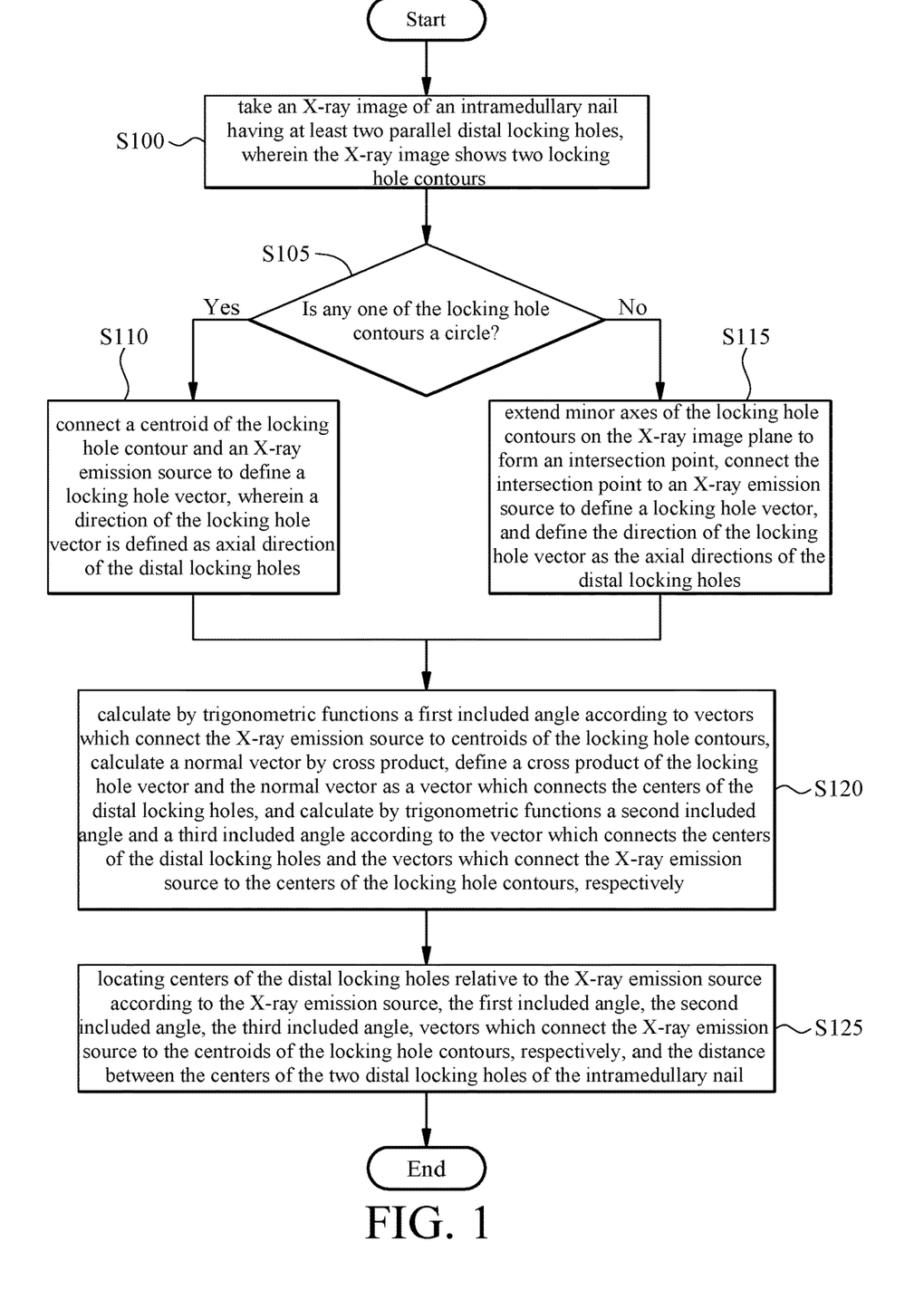
FIG. 1 is a first flowchart of a method of locating a distal locking hole of an intramedullary nail according to the present invention.

Referring to FIG. 1, it is shown a first flowchart of a method of locating distal locking holes of an intramedullary nail according to the present invention. With the method, the distal locking holes of an intramedullary nail can be quickly located in terms of axial directions and positions. The method works in conjunction with a processor and is described below.

Figure 2A:
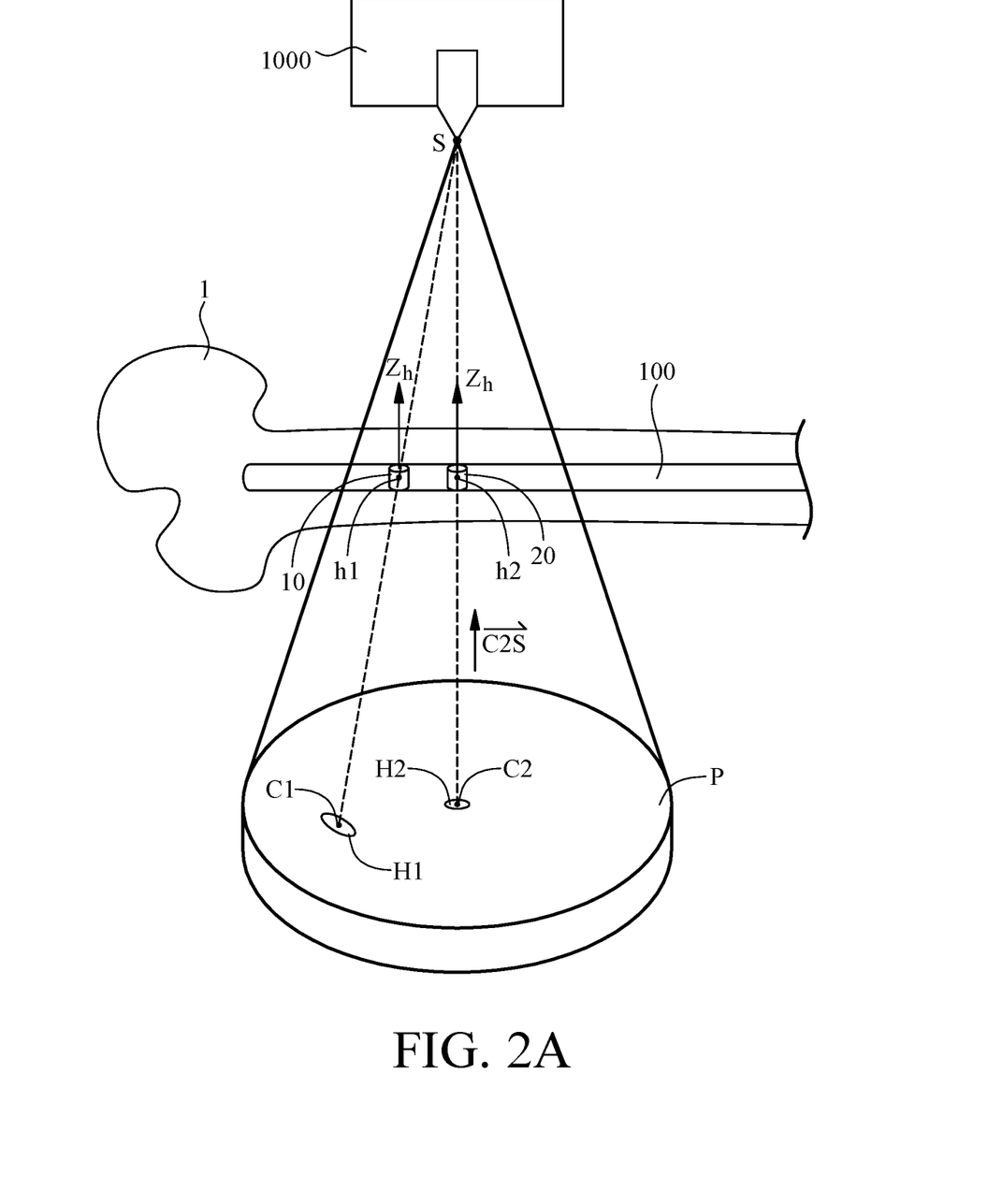
FIG. 2A is a schematic view of taking an X-ray image of an intramedullary nail in step S100 of the method according to the present invention.
Figure 2B:
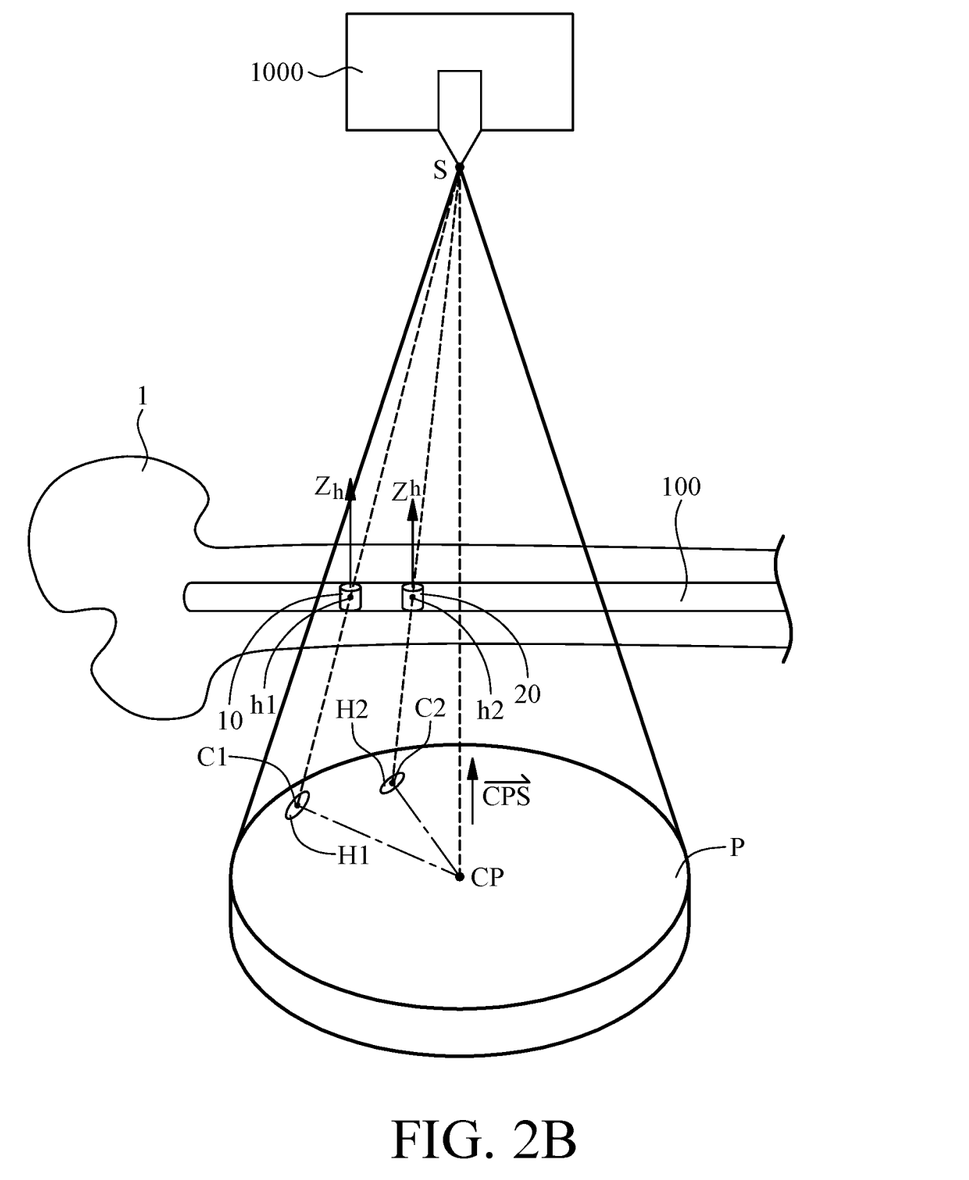
FIG. 2B is a schematic view of taking another X-ray image of the intramedullary nail in step S100 of the method according to the present invention.

In step S100 of the method, an intramedullary nail 100 with at least two parallel distal locking holes is implanted into a bone 1. An X-ray image-taking device 1000 takes an X-ray image P of the bone 1, and thus the X-ray image P shows the contours of the two distal locking holes. Referring to FIG. 2A and FIG. 2B, for illustrative sake, the schematic views show the bone 1 rather than the whole human body. The two parallel distal locking holes are defined with first locking hole 10 and second locking hole 20, respectively. Referring to FIG. 2A and FIG. 2B, the contour of the two distal locking holes shown in the X-ray image P are first locking hole contour H1 and second locking hole contour H2, respectively.

Step S100 is followed by step S105. In step S105, the processor determines whether any one of the first locking hole contour H1 and second locking hole contour H2 is a circle. Go to step S110, if the determination is affirmative. Go to step S115, if the determination is negative. Referring to FIG. 2A, the first locking hole contour H1 is an ellipse, whereas the second locking hole contour H2 is a circle, and thus step S110 is carried out. Referring to FIG. 2B, both the first locking hole contour H1 and the second locking hole contour H2 are ellipses, and thus step S115 is carried out.

In step S110, the processor creates a locking hole vector $\overrightarrow{C2S}$ by connecting centroid C2 of a locking hole contour, for example, the second locking hole contour H2, and an X-ray emission source S of the X-ray image-taking device 1000. With the second locking hole contour H2 being a circle, the X-ray emission source S points at the second locking hole contour H2, wherein the direction of the locking hole vector $\overrightarrow{C2S}$ is defined as axial direction Zh of the second locking hole 20. Step S110 is followed by step S120. The first locking hole 10 and the second locking hole 20 are parallel and thus have the same axial direction; hence, axial direction Zh of the second locking hole 20 is parallel to axial direction Zh of the first locking hole 10. Therefore, axial directions Zh of the first locking hole 10 and second locking hole 20 relative to the X-ray emission source S are definite.

Figure 3:
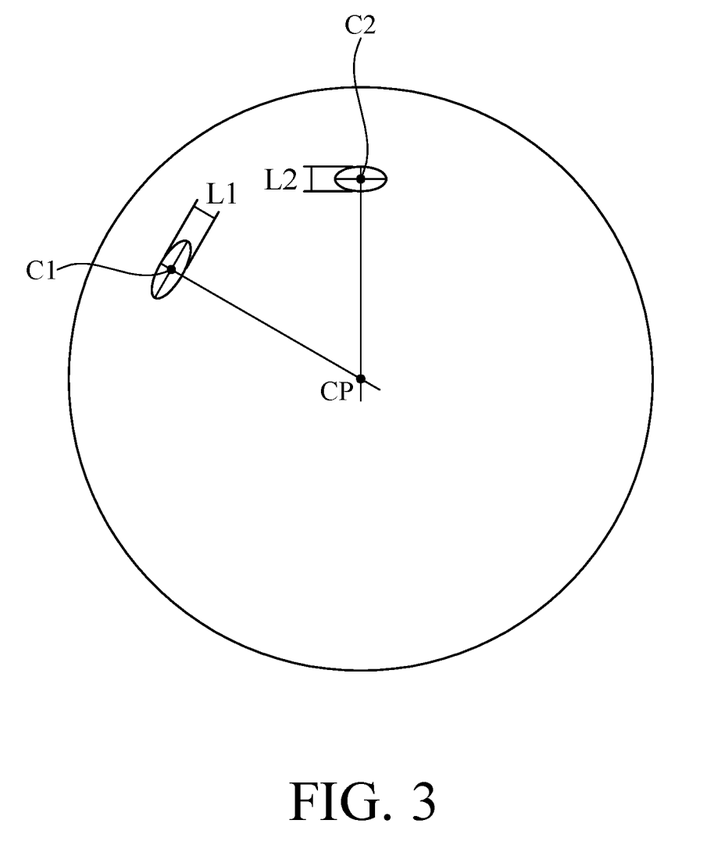
FIG. 3 is a top view of the X-ray image of FIG. 2B according to the present invention.

In step S115, on the X-ray image plane P (shown in FIG. 3), the processor extends minor axis L1 of first locking hole contour H1 and minor axis L2 of second locking hole contour H2 to form an intersection point CP. Referring to FIG. 2B, the intersection point CP is connected to an X-ray emission source S of the X-ray image-taking device 1000 to thereby define a locking hole vector $\overrightarrow{CPS}$, wherein the direction of the locking hole vector $\overrightarrow{CPS}$ is defined as axial direction Zh of the first locking hole 10 and second locking hole 20. Step S115 is followed by step S120. In step S120, C1 denotes the center of the first locking hole contour H1, whereas C2 denotes the center of the second locking hole contour H2. Hence, axial directions Zh of the first locking hole 10 and second locking hole 20 relative to the X-ray emission source S are definite.

Figure 4:
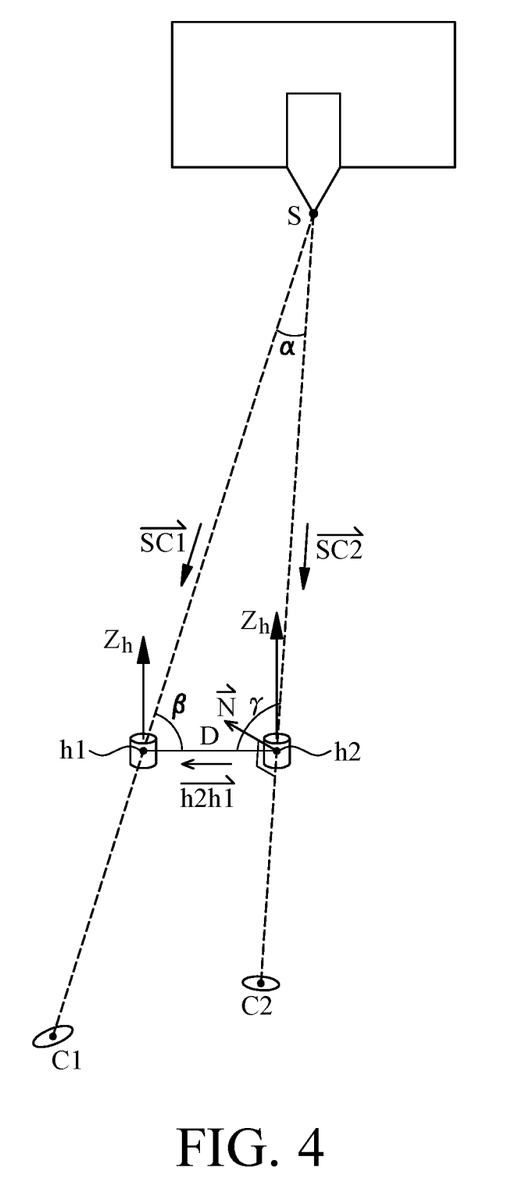
FIG. 4 is a schematic view of step S120 of the method according to the present invention.

Step S120 is illustrated with FIG. 2B and FIG. 4 and described below.

The purpose of step S120 is to locate center h1 of first locking hole 10 and center h2 of second locking hole 20 relative to the X-ray emission source S. In step S120, the processor connects the X-ray emission source S to the centroid C1 of first locking hole contour H1 and centroid C2 of second locking hole contour H2 to form vectors $\overrightarrow{SC1}$, $\overrightarrow{SC2}$, calculates a first included angle α by trigonometric functions, and defines vector $\overrightarrow{h2h1}$ which connects center h1 of first locking hole 10 and center h2 of second locking hole 20 of the intramedullary nail 100. Referring to FIG. 4, since a plane can be defined by the X-ray emission source S, the centroid C1 and the centroid C2, a normal vector $\vec{N}$ of the plane can be calculated by the cross product of vectors $\overrightarrow{SC1}$, $\overrightarrow{SC2}$. The normal vector $\vec{N}$ is also perpendicular to the vector $\overrightarrow{h2h1}$ that belongs to the plane. With the vector $\overrightarrow{h2h1}$ being perpendicular to the locking hole vector $\overrightarrow{CPS}$ and the normal vector $\vec{N}$, the cross product of the locking hole vector $\overrightarrow{CPS}$ and the normal vector $\vec{N}$ can be defined as a vector which connects the centers h2 and h1 of the distal locking holes, that is, the vector $\overrightarrow{h2h1}$. Given the vector $\overrightarrow{h2h1}$, to locate the center h1 of first locking hole 10 and center h2 of second locking hole 20 relative to the X-ray emission source S, it is necessary to calculate a second included angle β and a third included angle γ according to the vector $\overrightarrow{h2h1}$ and vectors $\overrightarrow{SC1}$, $\overrightarrow{SC2}$ by trigonometric functions.

In step S125, given the first included angle α, the second included angle β and the third included angle γ, it is feasible to locate the center h1 of first locking hole 10 and the center h2 of second locking hole 20 relative to the X-ray emission source S according to the X-ray emission source S, vectors $\overrightarrow{SC1}$, $\overrightarrow{SC2}$ which connect the X-ray emission source S to the centroid C1 of first locking hole contour H1 and centroid C2 of second locking hole contour H2, respectively, and distance D between the center h1 of first locking hole 10 and center h2 of second locking hole 20 of the intramedullary nail 100. The distance D is predetermined, because it always depends on the model number of the intramedullary nail 100.

In conclusion, unlike the prior art, the present invention provides a method of locating distal locking holes of an intramedullary nail by using one and only one X-ray image.

According to the present invention, the axial directions of two distal locking holes relative to the X-ray emission source are identified in step S110 and step S115, whereas the positions of the two distal locking holes relative to the X-ray emission source are determined in step S125 such that a medical person can align the distal locking holes quickly and precisely so as to facilitate a drilling process. Furthermore, the convenience of using one and only one X-ray image is advantageously accompanied by the reduction of the radiation dose of X-ray which medical persons and the patient might otherwise be exposed to.

Correction of the image and image projection model of X-ray image-taking device can be carried out to the X-ray image-taking device 1000 before or during step S100 such that the axial directions and positions of the distal locking holes relative to the X-ray emission source can be precisely determined.

Figure 5:
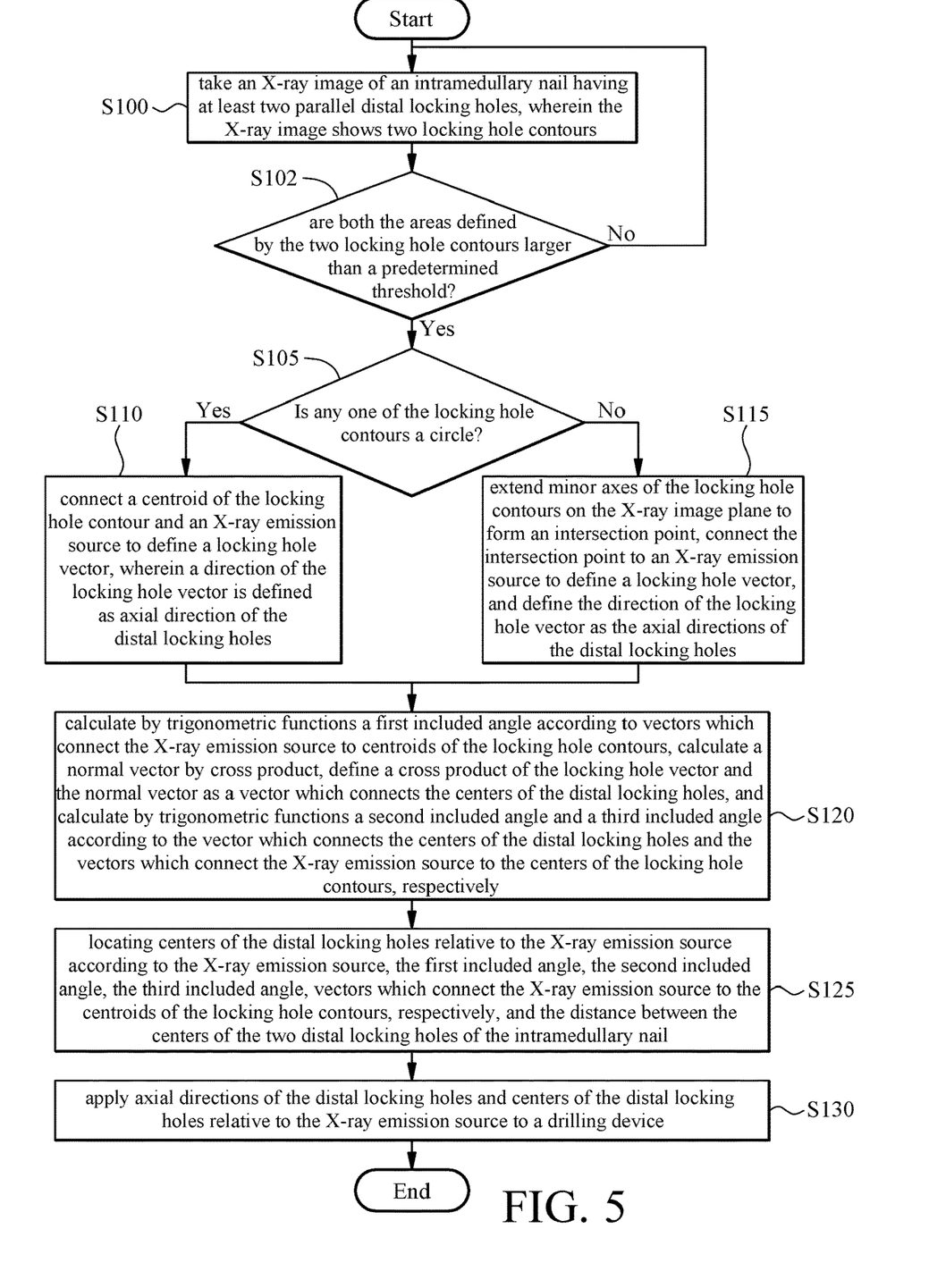
FIG. 5 is a second flowchart of the method of locating a distal locking hole of an intramedullary nail according to the present invention.

Referring to FIG. 5, there is shown a second flowchart of the method of locating distal locking holes of an intramedullary nail according to the present invention. The second flowchart includes all the steps of the first flowchart, step S130 which follows step S125, and step S102 which occurs between step S100 and step S105.

In step S130, the axial directions Zh of first locking hole 10 and second locking hole 20 as well as the positions of the center h1 of first locking hole 10 and center h2 of second locking hole 20 relative to the X-ray emission source S are applied and transformed to the coordinate system of a drilling device (not shown), thereby facilitating the drilling process carried out with the drilling device.

Step S102 involves determining whether both the areas defined by the first locking hole contour H1 and second locking hole contour H2 are larger than a predetermined threshold. Go to step S105, if the determination is affirmative. Go to step S100, if the determination is negative. One of the purposes of step S102 is to circumvent the situation where minor axes of the first and second locking hole contours H1, H2 cannot be identified as a result of step S115.

In conclusion, according to the present invention, a method of locating distal locking holes of an intramedullary nail requires using one and only one X-ray image has advantages as follows: calculate axial directions of two distal locking holes relative to the X-ray emission source and locate the two distal locking holes relative to the X-ray emission source such that the medical person can quickly and precisely locate the distal locking holes relative to the X-ray emission source to thereby facilitate a drilling process; and by taking one and only one X-ray image, it is feasible to reduce the radiation dose of X-ray which medical persons and a patient might otherwise be exposed to.

The present invention is disclosed above by preferred embodiments. However, persons skilled in the art should understand that the preferred embodiments are illustrative of the present invention only, but should not be interpreted as restrictive of the scope of the present invention. Hence, all equivalent modifications and replacements made to the aforesaid embodiments should fall within the scope of the present invention. Accordingly, the legal protection for the present invention should be defined by the appended claims.

What is claimed is:

1. A method of locating distal locking holes of an intramedullary nail to enable quick alignment, the method comprising the steps of:
   a) taking an X-ray image of an intramedullary nail having at least two parallel distal locking holes with an X-ray image-taking device, wherein the X-ray image shows two locking hole contours;
   b) determining, by a processor, a locking hole vector for the locking hole contours that are ellipses as being directed from a position of an intersection point of minor axes of the locking hole contours to a position of an X-ray emission source of the X-ray image-taking device, wherein the direction of the locking hole vector is defined as axial direction of the distal locking hole, and the intersection point is formed by extending the minor axes of the locking hole contours on an X-ray image plane indicating a corresponding plane of the X-ray image;
   c) calculating, by the processor, by trigonometric functions a first included angle according to source-to-centroid vectors which are directed from the position of the X-ray emission source to the respective centroids of the locking hole contours; calculating, by the processor, a normal vector by cross product of the source-to-centroid vectors; defining, by the processor, a cross product of the locking hole vector and the normal vector as a vector which is defined by the centers of the distal locking holes; and calculating, by the processor, by trigonometric functions a second included angle and a third included angle according to the vector which is defined by the centers of the distal locking holes and the source-to-centroid vectors which are directed from the position of the X-ray emission source to the centers of the locking hole contours, respectively;
   d) determining, by the processor, centers of the distal locking holes relative to the X-ray emission source according to the X-ray emission source, the first included angle, the second included angle, the third included angle, the source-to-centroid vectors which are directed from the position of the X-ray emission source to the centroids of the locking hole contours, respectively, and a distance between the centers of the two distal locking holes of the intramedullary nail; and
   e) applying the axial directions of the distal locking holes and the centers of the distal locking holes relative to the X-ray emission source to a drilling device so as to facilitate a drilling process carried out with the drilling device.

* * * * *